United States Patent [19]

Tegeler et al.

[11] Patent Number: 4,514,410
[45] Date of Patent: Apr. 30, 1985

[54] SUBSTITUTED 8-PHENYLISOXAZOLO[4,3-E][1,4]DIAZEPIN-5-ONES

[75] Inventors: John J. Tegeler, Bridgewater; Craig J. Diamond, Budd Lake, both of N.J.

[73] Assignee: Hoechst-Roussel Pharmaceuticals Inc., Somerville, N.J.

[21] Appl. No.: 615,857

[22] Filed: May 31, 1984

[51] Int. Cl.³ .................. A61K 31/55; C07D 498/04; C07D 261/14
[52] U.S. Cl. ............... 514/221; 260/239.3 B; 548/245
[58] Field of Search ............... 260/239.3 B; 424/272

[56] References Cited

U.S. PATENT DOCUMENTS 4,172,079 10/1979 Love .................................. 548/245

OTHER PUBLICATIONS

Dal Piaz et al., "Synthesis", pp. 664–665, (Oct. 1975), Communications.
Jaunin, "Helv. Chim. Acta", (1974), vol. 57 (7), pp. 1934–1942.
Otsuji et al., "Bull. Chem. Soc. Japan", vol. 44, pp. 223–226 (1971).

Primary Examiner—Robert T. Bond
Attorney, Agent, or Firm—James R. Cartiglia

[57] ABSTRACT

This invention relates to substituted 8-phenylisoxazolo[4,3-e][1,4]diazepin-5-ones of the formula

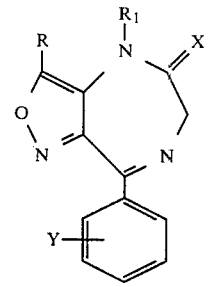

wherein R is lower alkyl; $R_1$ is hydrogen, amino alkyl, propargyl and lower alkyl; X is oxygen and sulfur; and Y is halogen, trifluoromethyl, lower alkyl, lower alkoxy and hydrogen. The compounds of this invention display useful anxiolytic and anticonvulsant activites.

73 Claims, No Drawings

SUBSTITUTED 8-PHENYLISOXAZOLO[4,3-E][1,4]DIAZEPIN-5-ONES

To the best of our knowledge the compounds of the present invention have not heretofore been described or suggested.

The compounds of the present invention have the general formula (I)

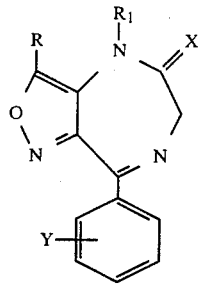

wherein R is lower alkyl; $R_1$ is hydrogen, propargyl, lower alkyl and amino alkyl of the formula

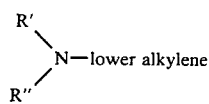

where R' and R" are the same or different and are hydrogen and lower alkyl such as diethylaminoethyl; X is oxygen and sulfur; and Y is hydrogen, halogen, lower alkyl, lower alkoxy and trifluoromethyl.

In the above definitions the term "lower" means the group it is describing contains from 1 to 6 carbon atoms. The term "alkyl" refers to a straight or branched chain hydrocarbon containing no unsaturation, e.g. methyl, ethyl, isopropyl, 2-butyl, neopentyl, n-hexyl, etc.; the term "propargyl" refers to a three carbon chain containing a methylene carbon attached to a carbon-carbon triple bond ($-CH_2C\equiv CH$); the term "alkoxy" refers to an univalent radical composed of an alkyl group linked through an oxygen atom having its free valence bond therefrom, e.g., methoxy ($-O-CH_3$), ethoxy ($-O-CH_2-CH_3$); the term "alkylene" refers to a bivalent radical of the lower branched or unbranched alkyl groups it is derived from, having valence bonds from two terminal carbons thereof, e.g., ethylene ($-CH_2CH_2-$), propylene ($-CH_2CH_2CH_2-$), isopropylene

etc., the term "amino" refers to the group $NH_2$ wherein one or both hydrogen atoms may be substituted with a lower alkyl; the term "nitro" refers to the univalent group $NO_2$ having a free valence bond through nitrogen; and the term "halogen" refers to a member of the family consisting of fluorine, chlorine, bromine and iodine.

Preferred compounds of this invention are those where R is methyl and X is oxygen.

The compounds of the invention are prepared in the following manner. The substitutents X, Y, R and $R_1$ are as defined above unless indicated otherwise.

A compound of the formula (II)

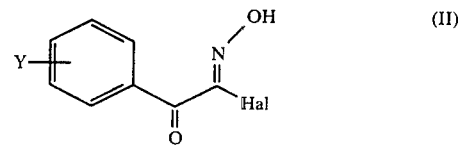

wherein Hal is a halogen is selected. Compound II is reacted in a conventional manner with an α-nitromethylketone of the formula (IIa)

and triethylamine, typically in the presence of a solvent, e.g. ethanol or tetrahydrofuran, at a temperature of 25° C. to reflux of solvent, for a time period of 1 to 24 hours to form Compound III having the formula

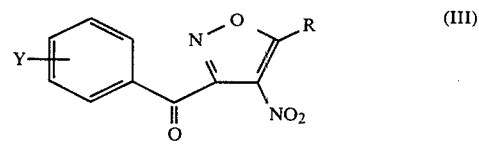

Compound III is reduced in a conventional manner, as for example with a metal salt, such as tin (II) chloride and an acid, such as hydrochloric acid, with or without a cosolvent, such as acetic acid or tetrahydrofuran, at a temperature ranging from 0° C. to reflux of solvent for about 1 to 24 hours to form Compound IV having the formula

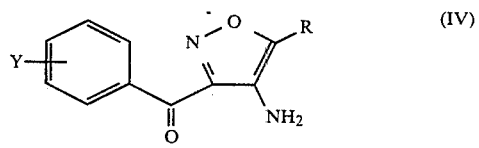

Compound IV is reacted in a conventional manner with a haloacetylhalide in a polar solvent, e.g., dichloromethane, in the presence of a base such as sodium carbonate or sodium bicarbonate. Typically, the reaction is carried out at 0° to 25° C. for ½ to 1 hour, to form Compound V having the formula

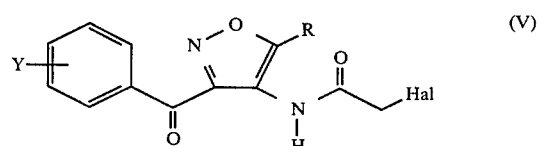

wherein Hal is a halogen. Compound V is cyclized by reaction in methanol with ammonia and then partitioned and extracted. The resultant product is then reacted in methanol with acetic acid and refluxed for a time period of 3 to 6 hours to form Compound VI having the formula

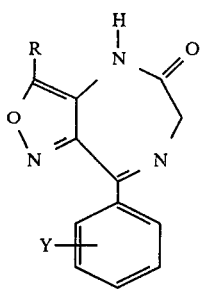

(VI)

Compound VI may then be further reacted with a lower alkylamino lower alkylene chloride or a lower alkyl iodide to form Compound VII having the formula

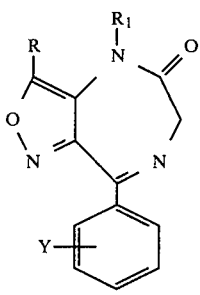

(VII)

Compound VII may be reacted with a sulfurating reagent, such as phosphorus pentasulfide, to form Compound VIII having the formula

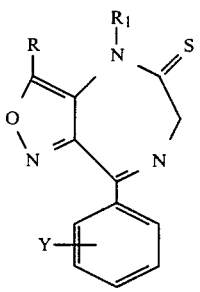

(VIII)

The utility of the compounds of the present invention in the treatment of convulsions in patients is demonstrated by their ability to inhibit extensor tonus induced by electroshock in mice, a standard assay of useful anti-convulsant properties. The anti-convulsant activity of some of the compounds of this invention expressed in terms of the effective dose for 50% inhibition of extensor tonus in mg/kg of body weight in electroshocked mice is given in Table I.

TABLE I

| Compound | $ED_{50}$ for Inhibition of Extensor Tonus |
|---|---|
| 3,4-dimethyl-8-phenylisoxazolo[4,3-e]-[1,4]diazepin-5-one | 25.1 |
| 3,4-dimethyl-8-(2-chlorophenyl)isoxazolo-[4,3-e] [1,4]diazepin-5-one | 35.6 |
| 3,4-dimethyl-8-(2-fluorophenyl)isoxazolo-[4,3-e] [1,4]diazepin-5-one | 79.8 |

TABLE I-continued

| Compound | $ED_{50}$ for Inhibition of Extensor Tonus |
|---|---|
| acetazolamide (standard) | 29.1 |

These data indicate that the compounds of the present invention are useful as anticonvulsants in mammals.

The compounds of the invention are also useful as anxiolytic agents due to their ability to reduce anxiety in mammals. Anxiolytic activity is measured as the average conflict response ratio (drug:control) at 40 mg/kg of body weight. The anxiolytic activity of some of the compounds of this invention is given in Table II.

TABLE II

| Compound | Average Conflict Response Ratio |
|---|---|
| 3,4-dimethyl-8-phenylisoxazolo[4,3-e]-[1,4]diazepin-5-one | 31.7 |
| 3,4-dimethyl-8-(2-chlorophenyl)isoxazolo-[4,3-e] [1,4]diazepin-5-one | 18.2 |
| 3,4-dimethyl-8-(2-fluorophenyl)isoxazolo-[4,3-e] [1,4]diazepin-5-one | 11.2 |
| chlordiazepoxide @ 20 mg/kg (standard) | 32.6 |

This data indicates that the compounds of the present invention are useful as anxiolytics in mammals.

Effective amounts of the compounds of the present invention may be administered to a subject by one of various methods, for example, orally as in capsules or tablets, parenterally in the form of sterile solutions or suspensions, and in some cases intravenously in the form of sterile solutions. The compounds of the invention, while effective themselves, may be formulated and administered in the form of their pharmaceutically acceptable acid addition salts for purposes of stability, convenience of crystallization, increased solubility and the like.

Preferred pharmaceutically acceptable acid addition salts include those derived from inorganic acids such as hydrochloric, hydrobromic, sulfuric, nitric, phosphoric, perchloric acids and the like as well as organic acids such as tartaric, citric, acetic, succinic, maleic, fumaric acids and the like.

The compounds of the present invention may be administered orally, for example, with an inert diluent or with an edible carrier. They may be enclosed in gelatin capsules or compressed into tablets. For the purpose of oral therapeutic administration, the compounds may be incorporated with excipients and used in the from of tablets, troches, capsules, elixirs, suspensions, syrups, wafers, chewing gums and the like. These preparations should contain at least 4% of the substituted 8-arylisoxazolo[4,3-e][1,4]diazepin-5-ones of this invention, the active ingredient, but may be varied depending upon the particular form and may conveniently be between 4% to about 70% of the weight of the unit. The amount of the compound present in such compositions is such that a suitable dosage will be obtained. Preferred compositions and preparations according to the present invention are prepared so that an oral dosage unit form contains between 5.0–300 milligrams of the substituted 8-arylisoxazolo[4,3-e][1,4]diazepin-5-ones of this invention. The tablets, pills, capsules, troches and the like may also contain the following adjuvants: a binder such as microcrystalline cellulose, gum tragacanth or gelatin; an excipient such as starch or lactose; a distintegrating agent such as alginic acid, Primogel, corn starch and the like; a lubricant such as magnesium stearate or Sterotex; a glidant such as colloidal silicon dioxide; and a sweetening agent such as sucrose or saccharin may be added or a flavoring agent such as peppermint, methyl salicylate or orange flavoring. When the dosage unit form is a capsule, it may contain, in addition to materials of the above type, a liquid carrier such as a fatty oil. Other dosage unit forms may contain other various matrials which modify the physical form of the dosage unit, for example, as coating. Thus, tablets or pills may be coated with sugar, shellac, or other enteric coating agents. A syrup may contain, in addition to the present compound, sucrose as a sweetening agent and certain preservatives, dyes and colorings and flavors. Materials used in preparing these various compositions should be pharmaceutically pure and non-toxic in the amounts used.

For the purpose of parenteral therapeutic administration, the compounds of the present invention may be incorporated into a solution or suspension. These preparations should contain at least 0.1% of the substituted 8-arylisoxazolo[4,3-e][1,4]-diazepin-5-ones of this invention, but may be varied to be between 0.1 and about 50% of the weight thereof. The amount of the inventive compound present in such compositions is such that a suitable dosage will be obtained. Preferred compositions and preparations according to the present invention are prepared so that a parenteral dosage unit contains between 5.0 to 100 milligrams of the substituted 8-arylisoxazolo[4,3-e][1,4]-diazepin-5-ones of this invention.

The solutions or suspensions may also include the following adjuvants: a sterile diluent such as water for injection, saline solution, fixed oils, polyethylene glycols, glycerine, propylene glycol or other synthetic solvents; antibacterial agents such as benzyl alcohol or methyl paraben; antioxidants such as ascorbic acid or sodium bisulfite; chelating agents such as ethylene diaminetetraacetic acid; buffers such as acetates, citrates or phosphates; and agents for the adjustment of tonicity such as sodium chloride or dextrose. The parenteral preparation can be enclosed in ampules, disposable syringes or multiple dose vials made of glass or plastic.

Other compounds of the invention include:
4-(2-Diethylaminoethyl)-3-ethyl-8-(2,6-difluorophenyl)isoxazolo[4,3-e][1,4]diazepin-5-one;
4-(2-Diethylaminoethyl)-3-ethyl-8-[2-(trifluoromethyl)phenyl]isoxazolo[4,3-e][1,4]diazepin-5-one;
4-(2-Diethylaminoethyl)-3-ethyl-8-(2-fluorophenyl)isoxazolo[4,3-e][1,4]diazepin-5-one;
4-(2-Diethylaminoethyl)-3-ethyl-8-(2-chlorophenyl)isoxazolo[4,3-e][1,4]diazepin-5-one;
4-(2-Diethylaminoethyl)-3-ethyl-8-phenylisoxazolo[4,3-e][1,4]diazepin-5-one;
3-Ethyl-8-(2,6-difluorophenyl)isoxazolo[4,3-e][1,4]diazepin-5-one;
3-Ethyl-8-[2-(trifluoromethyl)phenyl]isoxazolo[4,3-e][1,4]diazepin-5-one;
3-Ethyl-8-(2-fluorophenyl)isoxazolo[4,3-e][1,4]diazepin-5-one;
3-Ethyl-8-(2-chlorophenyl)isoxazolo[4,3-e][diazepin-5-one;
3-Ethyl-8-phenylisoxazolo[4,3-e][1,4]diazepin-5-one;
3-Ethyl-4-methyl-(2,6-difluorophenyl)isoxazolo[4,3-e][1,4]diazepin-5-one;
3-Ethyl-4-methyl-8-[2-(trifluoromethyl)phenyl]isoxazolo[4,3-e][1,4]diazepin-5-one;
3-Ethyl-4-methyl-8-(2-fluorophenyl)isoxazolo[4,3-e][1,4]diazepin-5-one;
3-Ethyl-4-methyl-8-(2-chlorophenyl)isoxazolo[4,3-e][1,4]diazepin-5-one;
3-Ethyl-4-methyl-8-phenylisoxazolo[4,3-e][1,4]diazepin-5-one;
4-(2-Diethylaminoethyl)-3-methyl-8-(2-methylphenyl)isoxazolo[4,3-e][1,4]diazepin-5-one;
3-Methyl-8-(2-methylphenyl)isoxazolo[4,3-e][1,4]diazepin-5-one;
3,4-Dimethyl-8-(2-methylphenyl)isoxazolo[4,3-e][1,4]diazepin-5-one;
4-(2-Diethylaminoethyl)-3-ethyl-8-(2-methylphenyl)isoxazolo[4,3-e][1,4]diazepin-5-one;
3-Ethyl-8-(2-methylphenyl)isoxazolo[4,3-e][1,4]diazepin-5-one;
3-Ethyl-4-methyl-8-(2-methylphenyl)isoxazolo[4,3-e][1,4]-diazepin-5-one;
3,4-Dimethyl-8-(2-methoxyphenyl)isoxazolo[4,3-e][1,4]diazepin-5-one;
3-Methyl-8-(2,6-difluorophenyl)isoxazolo[4,3-e][1,4]diazepin-5-one;
3,4-Dimethyl-8-(2,6-difluorophenyl)isoxazolo[4,3-e][1,4]diazepin-5-one;
3-Ethyl-4-(2-propynyl)-8-(2-fluorophenyl)isoxazolo[4,3-e][1,4]diazepin-5-one;
3-Ethyl-4-(2-propynyl)-8-(2,6-difluorophenyl)isoxazolo[4,3-e][1,4]diazepin-5-one;
3-Ethyl-4-(2-propynyl)-8-[2-(trifluoromethyl)phenyl]isoxazolo[4,3-e][1,4]diazepin-5-one;
3-Ethyl-4-(2-propynyl)-8-(2-chlorophenyl)isoxazolo[4,3-e][1,4]diazepin-5-one; and
3-Methyl-4-(2-propynyl)-8-(2-methylphenyl)isoxazolo[4,3-e][1,4]diazepin-5-one.

The following examples are for illustrative purposes and are not to be construed as limiting the invention disclosed herein. All temperatures are given in degrees centigrade unless specified to the contrary.

EXAMPLE I a. (5-Methyl-4-nitroisoxazol-3-yl)phenylmethanone

To a solution of 23 g (0.24 mole) nitroacetone in 400 ml ethanol at 0° C. was added dropwise a solution of 33 ml (0.24 mole) triethylamine in 92 ml ethanol. After cooling to −10° C., a solution of 43 g (0.24 mole) phenylglyoxylohydroxamyl chloride in 250 ml ethanol was added dropwise over 4 hours. The resulting mixture was stirred at room temperature overnight (about 16 hours). Concentration gave a gel that was partitioned between 200 ml water and 70 ml diethyl ether. The organic extract was washed thrice with water and dried (magnesium sulfate). Concentration gave 43 g of an oil that was chromatographed on a high pressure liquid chromatograph (HPLC) using toluene as an eluent to give an oil that solidified on standing. Recrystallization from ethanol gave 16.9 g (31%) of a solid, melting point 80°–82° C.

ANALYSIS: Calculated for $C_{11}H_8N_2O_4$: 56.90%C; 3.47%H; 12.07%N; Found: 56.73%C; 3.64%H; 12.15%N.

b. (4-Amino-5-methylisoxazol-3-yl)phenylmethanone

A solution of 47 g (0.20 mole) (5-methyl-4-nitroisoxazol-3-yl)phenylmethanone of Example Ia in 600 ml glacial acetic acid was added to a mixture of 360 g (1.60 moles) SnCl$_2$.2H$_2$O in one liter of concentrated hydrochloric acid and 200 ml acetic acid at room temperature. After stirring at room temperature overnight (about 16 hours), the reaction mixture was poured carefully into a well stirred mixture of 2400 g of 50% sodium hydroxide and 6500 ml ice with ice bath cooling. The resulting solids were collected by filtration, washed with water and partitioned between 600 ml 5% sodium hydroxide and 2 liters of 1:1 dichloromethane:diethyl ether. The aqueous was extracted thrice with diethyl ether and the organic extract was dried (magnesium sulfate). Concentration gave 26.3 g (65%) of an oil. Chromatography on high pressure liquid chromatograph (HPLC) using dichloromethane as an eluent of 4.0 g of this oil yielded 2.7 g (44%) of an oil that solidified on standing.

ANALYSIS: Calculated for C$_{11}$H$_8$N$_2$O$_2$: 65.33%C; 4.98%H; 13.86%N; Found: 65.39%C; 5.14%H; 13.93%N.

c.
N-(3-Benzoyl-5-methylisoxazol-4-yl)bromoacetamide

Bromoacetylbromide (40 g, 0.2 mole) was added slowly to a mixture of 20 g (0.1 mole) (4-amino-5-methylisoxazol-3-yl)-phenylmethanone of Example Ib in 500 ml dichloromethane with 200 ml of 2N sodium carbonate and 500 ml saturated sodium bicarbonate at 5° C. After stirring for 30 minutes the mixture was diluted with 400 ml dichloromethane and 400 ml water. The organics were washed with water and brine and dried (magnesium sulfate). Concentration gave 32 g of an oil which was chromatographed on high pressure liquid chromatograph (HPLC) using dichloromethane as an eluent to yield 23 g (71%) of a solid, melting point 89°–92° C.

ANALYSIS: Calculated for C$_{13}$H$_{11}$BrN$_2$O$_3$: 48.31%C; 3.43%H; 8.67%N; Found: 48.35%C; 3.50%H; 3.60%N.

d.
3-Methyl-8-phenylisoxazolo[4,3-e][1,4]diazepin-5-one

A solution of 20 g (62 mmoles) N-(3-benzoyl-5-methylisoxazol-4-yl)bromoacetamide of Example Ic in 600 ml methanol was added slowly at about −60° C. to 400 ml ammonia/methanol (15% weight (w)/volume (v)). The dry ice bath was removed and stirring continued at room temperature overnight (about 16 hours). Concentration gave a solid that was partitioned between dichloromethane and aqueous sodium carbonate solution. The aqueous was extracted thrice with diethyl ether and the combined organics were dried (magnesium sulfate). Concentration gave 17 g of an oil that was combined with 225 ml methanol and 7.1 ml acetic acid. The resulting mixture was refluxed for 5 hours. The cooled reaction mixture was treated with 40 ml saturated sodium bicarbonate solution and poured gradually into 1200 ml of water with stirring. The resultant precipitated solid was collected and dried to give 11.2 g of a solid, melting point 214°–218° C. Recrystallization from ethanol yielded 6.3 g (42%) of crystals, melting point 223°–225° C.

ANALYSIS: Calculated for C$_{13}$H$_{11}$N$_3$O$_2$: 64.72%C; 4.60%H; 17.42%N; Found: 65.05%C; 4.55%H; 17.59%N.

EXAMPLE II
3,4-Dimethyl-8-phenylisoxazolo[4,3-e][1,4]diazepin-5-one

To a solution of 4.5 g (18.7 mmoles) 3-methyl-8-phenylisoxazolo[4,3-e][1,4]diazepin-5-one of Example Id in 70 ml dimethylformamide (DMF) was added NaH, from washing 0.9 g (18.7 mmoles) 50% oil dispersion with hexane, under nitrogen (N$_2$) with ice bath cooling. After stirring for 15 minutes a homogeneous solution was obtained. To this was added a solution of 1.3 ml (20.8 mmoles) of methyl iodide in 10 ml DMF dropwise to maintain the reaction temperature below 5° C. The resulting mixture was poured into 300 ml of sodium bicarbonate solution and extracted six times with 200 ml portions of diethyl ether. The extract was washed thrice with 300 ml portions of water and dried (sodium sulfate). Concentration gave 4.4 g of a solid that was recrystallized from cyclohexane/toluene to give 2.6 g (55%) of crystals, melting point 118°–119.5° C.

ANALYSIS: Calculated for C$_{14}$H$_{13}$N$_3$O$_2$: 65.87%C; 5.13%H; 16.46%N; Found: 66.22%C; 5.31%H; 16.39%N.

EXAMPLE III
a.
(5-Methyl-4-nitroisoxazol-3-yl)-2-chlorophenylmethanone To a solution of nitroacetone (32 g, 300 mmoles) in tetrahydrofuran (THF) (600 ml) at 0° C. was added triethylamine (30.3 g, 300 mmoles) dropwise. A solution of 2-chlorophenylglyoxylohydroxyamyl chloride (65 g, 300 mmoles) in THF (300 ml) was added at 0° C. over 3 hours. The reaction mixture was stirred at room temperature overnight (about 16 hours). The mixture was filtered to remove triethylamine hydrochloride, the salts were washed with diethyl ether and the organics were combined and evaporated. The residue (83 g) was flash chromatographed with dichloromethane to give 67 g (84%) of an oil. This material (6 g) was flash chromatographed (ethyl acetate:hexane, 1:5) to yield 4.8 g (68%) of an oil.

ANALYSIS: Calculated for C$_{11}$H$_7$ClN$_2$O$_4$: 49.55%C; 2.65%H; 10.50%N; Found: 49.64%C; 2.79%H; 10.17%N.

b.
(4-Amino-5-methylisoxazol-3-yl)-2-chlorophenylmethanone

A solution of (5-methyl-4-nitroisoxazol-3-yl)-2-chlorophenylmethanone of Example IIIa (5.3 g, 20 mmoles) in tetrahydrofuran (THF) (25 ml) was added to a mixture of SnCl$_2$ 2H$_2$O (18 g, 80 mmoles) in concentrated hydrochloric acid (35 ml) and THF (20 ml) over 1 hour. After stirring overnight at room temperature (about 16 hours), the reaction mixture was poured into cold 10% sodium hydroxide (500 ml) with stirring and extracted with ethyl acetate. The extracts were washed with dilute sodium chloride and dried (sodium sulfate). Concentration gave an oil which was flash chromatographed (20% ethyl acetate:hexane) to yield 3.0 g (64%) of an oil that solidified. The resultant amine was triturated with cyclohexane (40 ml) to yield 2.4 g (51%) of a powder, melting point 75°–78° C.

ANALYSIS: Calculated for $C_{11}H_9ClN_2O_2$: 55.83%C; 3.84%H; 11.83%N; Found: 55.88%C; 3.96%H; 11.85%N.

C.
N-[3-(2-Chlorobenzoyl)-5-methylisoxazol-4-yl]bromoacetamide

Bromoacetylbromide (42 g, 210 mmoles) was added slowly to a mixture of (4-amino-5-methylisoxazol-3-yl)-2-chlorophenylmethanone of Example IIIb (24.8 g, 105 mmoles) in dichloromethane (300 ml) with 2N sodium carbonate (200 ml) and saturated sodium bicarbonate (500 ml) at 5° C. After stirring for 1 hour, the mixture was diluted with dichloromethane (400 ml) and water (400 ml). The organics were washed with water, saturated sodium chloride, dried (sodium sulfate) and evaporated to give 36 g of an oil. The residue (5.2 g) was flash chromatographed (25% ethyl acetate:hexane) to yield 4.5 g (85%) of an oil.

ANALYSIS: Calculated for $C_{13}H_{10}BrClN_2O_3$: 43.66%C; 2.82%H; 7.83%N; Found: 43.64%C; 2.96%H; 7.61%N.

d.
3-Methyl-8-(2-chlorophenyl)isoxazolo[4,3-e][1,4]diazepin-5-one

A solution of N-[3-(2-chlorobenzoyl)-5-methylisoxazol-4-yl]bromoacetamide of Example IIIc (10.7 g, 30 mmoles) in methanol (250 ml) was added slowly to a solution of ammonia (15% w/v) in methanol (250 ml) at −60° C. The cooling bath was removed and stirring continued at room temperature overnight (about 16 hours). Concentration gave an oily residue that was dissolved in dichloromethane and washed with 5% sodium carbonate. Concentration gave a solid that was combined with acetic acid (3.5 ml) in methanol (110 ml) and the mixture was refluxed for 3 hours. The reaction mixture was made alkaline with 5% sodium carbonate and the precipitate was collected to yield a solid. Recrystallization from ethanol (500 ml) yielded 2.4 g (29%) of crystals, melting point 258°-260° C.

ANALYSIS: Calculated for $C_{13}H_{10}ClN_3O_2$: 56.63%C; 3.66%H; 15.24%N; Found: 56.54%C; 3.76%H; 15.33%N.

EXAMPLE IV
3,4-Dimethyl-8-(2-chlorophenyl)isoxazolo[4,3-e][1,4]diazepin-5-one A solution of 3-methyl-8-(2-chlorophenyl)isoxazolo[4,3-e]-[1,4]diazepin-5-one of Example IIId (7.9 g, 28.7 mmoles) in dimethylformamide (DMF) (80 ml) was added to a suspension of hexane-washed sodium hydride (1.24 g, 25.8 mmoles, 50% oil dispersion) in DMF (50 ml) at 5° C. After warming to 20° C., methyl iodide (1.97 ml, 31.6 mmoles) was added. The reaction solution was poured into dilute sodium bicarbonate (600 ml) with stirring. The precipitate was extracted with ethyl acetate, the organic solution was washed with water, saturated sodium chloride, and dried (sodium sulfate). Concentration gave a solid (8.8 g) which was chromatographed by high pressure liquid chromatography (HPLC) (8% ethyl acetate:dichloromethane) to yield 7.2 g (77%) of a solid, melting point 136°-138° C.

ANALYSIS: Calculated for $C_{14}H_{12}ClN_3O_2$: 58.04%C; 4.18%H; 14.50%N; Found: 57.93%C; 4.33%H; 14.38%N.

EXAMPLE V
a.
(5-Methyl-4-nitroisoxazol-3-yl)-4-chlorophenylmethanone To a solution of nitroacetone (5.1 g, 50 mmoles) in tetrahydrofuran (THF) (90 ml) at 0° C. was added a solution of triethylamine (6.9 ml, 50 mmoles) in THF (15 ml). After cooling to −10° C., a solution of 4-chlorophenylgloxylohydroxamyl chloride (10.9 g, 50 mmoles) in THF (50 ml) was added dropwise over 2 hours. The reaction mixture was filtered and the precipitate washed with diethyl ether. The combined organics were evaporated to a crystalline solid which was recrystallized from ethanol (400 ml) to yield 6.4 g (48%) of a solid melting point 173°-175° C.

ANALYSIS: Calculated for $C_{11}H_7ClN_2O_4$: 49.55%C; 2.65%H; 10.50%N; Found: 49.55%C; 2.82%H; 10.51%N.

b.
(4-Amino-5-methylisoxazol-3-yl)-4-chlorophenylmethanone

A solution of (5-methyl-4-nitroisoxazol-3-yl)-4-chlorophenylmethanone of Example Va (5.3 g, 20 moles) in tetrahydrofuran (THF) (100 ml) was added to a mixture of $SnCl_2 \cdot 2H_2O$ (27 g, 120 mmoles) in concentrated hydrochloric acid (35 ml) and THF (11 ml) over 1 hour. After warming to room temperature, the reaction mixture was poured into cold 10% sodium hydroxide (500 ml) with stirring and extracted with ethyl acetate. The extracts were washed with dilute sodium chloride and dried (sodium sulfate). Concentration gave 3.7 g (78%) of a solid, which was flash chromatographed (20% ethyl acetate:hexane) to yield 2.9 g (62%) of a solid, melting point 84°-86° C.

ANALYSIS: Calculated for $C_{11}H_9ClN_2O_2$: 55.83%C; 3.84%H; 11.83%N; Found: 55.81%C; 3.95%H; 11.80%N.

c.
N-[3-(4-Chlorobenzoyl)-5-methylisoxazol-4-yl]bromoacetamide

Bromoacetyl bromide (39 g, 194 mmoles) was added slowly to a mixture of (4-amino-5-methylisoxazol-3-yl)-4-chlorophenylmethanone of Example Vb (22.9 g, 97 mmoles) in dichloromethane (200 ml) with 2N sodium carbonate (200 ml) and saturated sodium bicarbonate (300 ml) at 5° C. After stirring for 1 hour, the mixture was diluted with dichloromethane (400 ml) and water (400 ml). The organics were washed with water, saturated sodium chloride, dried (sodium sulfate) and evaporated to give 34 g of a solid. The residue (3.0 g) was flash chromatographed (25% ethyl acetate:hexane) to yield 2.4 g (80%) of a solid, melting point 107°-110° C.

ANALYSIS: Calculated for $C_{13}H_{10}BrClN_2O_3$: 43.66%C; 2.82%H; 7.83%N; Found: 43.76%; 2.82%H; 7.76%N.

d.
3,4-Dimethyl-8-(4-chlorophenyl)isoxazolo[4,3-e][1,4]-diazepin-5-one

A solution of N-[3-(4-chlorobenzoyl)-5-methylisoxazol-4-yl]-bromoacetamide of Example Vc (4.26 g, 15.5 mmoles) in dimethylformamide (DMF) (40 ml) was added to a suspension of hexane-washed sodium hydride (0.67 g, 14 mmoles, 50% oil dispersion) in DMF (40 ml) at 5° C. After warming to 20° C., methyl iodide (1.06 ml, 17 mmoles) was added. The reaction solution was poured into dilute sodium bicarbonate (600 ml) with stirring. The precipitate was extracted with ethyl acetate, the organic solution was washed with water, saturated sodium chloride, and dried (sodium sulfate). Concentration gave a residue (5.5 g) which was chromatographed by high pressure liquid chromatography (HPLC) (8% ethyl acetate:dichloromethane) to give a solid that was pulverized to yield 3.0 g (66%) of a powder, melting point 133°–145° C.

ANALYSIS: Calculated for $C_{14}H_{12}ClN_3O_2$: 58.04%C; 4.18%H; 14.50%N; Found: 58.16%C; 4.37%H; 14.28%N.

EXAMPLE VI a. (5-Methyl-4-nitroisoxazol-3-yl)-2-fluorophenylmethanone

To a solution of nitroacetone (30 g, 288 mmoles) in tetrahydrofuran (THF) (580 ml) at 0° C. was added triethylamine (40 ml, 288 mmoles) dropwise. A solution of 2-fluorophenylglyoxylohydroxamyl chloride (58 g, 288 mmoles) in THF (290 ml) was added at 0° C. over 2 hours. The reaction mixture was stirred at room temperature overnight (about 16 hours). The mixture was filtered to remove triethylamine hydrochloride, the salts were washed with diethyl ether, the organics were combined and evaporated. The residue (72 g) was flash chromatographed with toluene to give 42 g (58%) of an oil that solidified. Recrystallization of 3.0 g from cyclohexane (200 ml) gave 2.3 g (45%) of crystals, melting point 81°–83° C.

ANALYSIS: Calculated for $C_{11}H_7FN_2O_4$: 52.81%C; 2.83%H; 11.19%N; Found: 52.85%; 3.05%H; 11.23%N.

b. (4-Amino-5-methylisoxazol-3-yl)-2-fluorophenylmethanone

A solution of (5-methyl-4-nitroisoxazol-3-yl)-2-fluorophenylmethanone of Example VIa (6.2 g, 25 mmoles) in tetrahydrofuran (THF) (25 ml) was added to a mixture of $SnCl_2 \cdot 2H_2O$ (22.4 g, 100 mmoles) in concentrated hydrochloric acid (40 ml) and THF (20 ml) with ice-bath cooling over 1 hour. After warming to room temperature, the reaction mixture was poured into cold 10% sodium hydroxide (500 ml) with stirring and extracted with ethyl acetate. The extracts were washed with dilute sodium chloride and dried (sodium sulfate). Concentration gave an oil which was flash chromatographed (20% ethyl acetate:hexane) to yield 2.4 g (44%) of an oil that solidified.

ANALYSIS: Calculated for $C_{11}H_9FN_2O_2$: 60.00%C; 4.13%H; 12.72%N; Found: 59.59%C; 4.09%H; 12.64%N.

c. N-[3-(2-Fluorobenzoyl)-5-methylisoxazol-4-yl]bromoacetamide

Bromoacetyl bromide (32 g, 160 mmoles) was added slowly to a mixture of (4-amino-5-methylisoxazol-3-yl)-2-fluorophenylmethanone of Example VIb (32 g, 145 mmoles) in dichloromethane (300 ml) with 2N sodium carbonate (100 ml) and saturated sodium bicarbonate (150 ml) at 10° C. After stirring for 1 hour, the mixture was diluted with dichloromethane (400 ml) and water (400 ml). The organics were washed with water, saturated sodium chloride, dried (sodium sulfate) and evaporated to give 49 g of an oil. The residue was flash chromatographed (25% ethyl acetate:hexane) to yield 47 g of an oil that solidified on standing. Trituration of the solid (3.0 g) with 20% ethyl acetate:hexane (25 ml) yielded 2.15 g (69%) of powder, melting point 94°–96° C.

ANALYSIS: Calculated for $C_{13}H_{10}BrFN_2O_3$: 45.77%C; 2.96%H; 8.21%N; Found: 45.44%C; 3.01%H; 8.11%N.

d. 3-Methyl-8-(2-fluorophenyl)isoxazolo[4,3-e][1,4]-diazepin-5-one

A solution of N-[3-(2-fluorobenzoyl)-5-methylisoxazol-4-yl]bromoacetamide of Example VIc (36.5 g, 107 mmoles) in tetrahydrofuran (THF) (150 ml) was added to a solution of ammonia (22% w/v) in methanol (900 ml) at −60° C. The cooling bath was removed and stirring continued at room temperature overnight (about 16 hours). Concentration gave a solid that was dissolved in methanol (500 ml) and acetic acid (15 ml). The mixture was refluxed for 6 hours and concentrated in vacuo. The residue was poured into dilute sodium carbonate, extracted with ethyl acetate, dried (sodium sulfate), and evaporated to a solid. The material was flash chromatographed (50% ethyl acetate:hexane) to yield 21 g of a solid. Recrystallization of 3.0 g from 1-propanol (150 ml) yielded 2.1 g (53%) of crystals, melting point 212°–214° C.

ANALYSIS: Calculated for $C_{13}H_{10}FN_3O_2$: 60.23%C; 3.90%H; 16.20%N; Found: 60.72%C; 4.08%H; 16.19%N.

EXAMPLE VII

3,4-Dimethyl-8-(2-fluorophenyl)isoxazolo[4,3-e][1,4]diazepin-5-one

A solution of 3-methyl-8-(2-fluorophenyl)isoxazolo[4,3-e]-[1,4]diazepin-5-one of Example VId (5.2 g, 20 mmoles) in dimethylformamide (DMF) (55 ml) was added to a suspension of hexane-washed sodium hydride (0.86 g, 18 mmoles, 50% oil dispersion) in DMF (50 ml) at 5° C. After warming to 20° C., methyl iodide (1.4 ml, 22 mmoles) was added. The resulting solution was poured into dilute sodium bicarbonate and extracted with ethyl acetate. The organic solution was washed with water, saturated sodium chloride, and dried (sodium sulfate). Concentration gave a solid (4.9 g) which was chromatographed by high pressure liquid chromatography (HPLC) (8% ethyl acetate:dichloromethane) to yield 3.6 g of a solid. Recrystallization from ethanol (100 ml) yielded 2.7 g (50%) of a solid, melting point 174°–175° C.

ANALYSIS: Calculated for $C_{14}H_{12}FN_3O_2$: 61.53%C; 4.44%H; 15.37%N; Found: 61.44%C; 4.52%H; 15.36%N.

EXAMPLE VIII

4-(2-Diethylaminoethyl)-8-(2-fluorophenyl)-3-methylisoxazolo-[4,3-e][1,4]diazepin-5-one A solution of 3-methyl-8-(2-fluorophenyl)isoxazolo-[4,3-e][1,4]diazepin-5-one of Example VII (3.9 g, 15 mmoles) in dimethylformamide (DMF) (40 ml) was added to a suspension of hexane-washed sodium hydride (0.65 g, 13.5 mmoles, 50% oil dispersion) in DMF (40 ml at 5° C.). After warming to 20° C., freshly distilled 2-diethylaminoethyl chloride (3.7 g, 27.4 mmoles) was added dropwise. The reaction solution was stirred at 20° C. and poured into dilute sodium carbonate with stirring. The mixture was extracted with ethyl acetate, the organic extract was washed with water, saturated sodium chloride and then dried (sodium sulfate). Concentration gave an oily residue (5.2 g) which was flash chromatographed (5% methanol:dichloromethane) to yield 2.9 g (54%) of an oil.

ANALYSIS Calculated for $C_{19}H_{23}FN_4O_2$: 58.21%C; 5.75%H; 11.80%N; Found: 58.36%C; 5.90%H; 11.89%N.

EXAMPLE IX a. 2-(Trifluoromethyl)phenylglyoxylohydroxamyl bromide

A solution of bromine (81 ml, 1.6 moles) in dichloromethane (80 ml) was added over 1 hour to a solution of 2-(trifluoromethyl)acetophenone (300 g, 1.6 moles) in anhydrous diethyl ether (2 liters). The reaction solution was concentrated in vacuo. The resulting liquid was dissolved in tetrahydrofuran (2.5 liters) and methyl sulfide (176 ml, 2.4 moles) was added. The solution was allowed to stand at room temperature for 5 days. The crystals were filtered to yield 240 g (46%) of dimethyl-2-(trifluoromethyl)phenacylsulfonium bromide, melting point 134°–136° C. A mixture of the sulfonium salt (240 g, 0.73 moles) and isopropyl nitrite (155 ml, 1.46 moles) was stirred in dichloromethane (2 liters) for four days at room temperature. The volatiles were evaporated in vacuo and the residue was dissolved in diethyl ether (2 liters). The organic solution was washed four times with 500 ml portions of water, saturated sodium chloride, dried (sodium sulfate) and evaporated to give an oil that crystallized on standing. Recrystallization from carbon tetrachloride gave 147 g (31% overall) of a solid, melting point 117°–118° C.

ANALYSIS: Calculated for $C_9H_5BrF_3NO_2$: 36.51%C; 1.71%H; 4.73%N; Found: 36.40%C; 1.74%H; 4.72%N.

b. (5-Methyl-4-nitroisoxazol-3-yl)-2-(trifluoromethyl)-phenylmethanone

To a solution of nitroacetone (45 g, 437 mmoles) in tetrahydrofuran (THF) (1 liter) at 5° C. was added triethylamine (61 ml, 437 mmoles) dropwise. A solution of 2-(trifluoromethyl)phenylglyoxylohydroxamyl bromide of Example IXa (129 g, 437 mmoles) in THF (440 ml) was added at 5° C. over 1 hour. The reaction mixture was stirred at room temperature overnight (about 16 hours). The mixture was filtered to remove triethylamine hydrochloride, the salts were washed with diethyl ether, the organics were combined and concentrated to 300 ml volume. Concentration of 12 ml of this solution gave a residue (5.2 g) that was flash chromatographed (20% ethyl acetate:hexane) to yield 2.8 g (54%) of a powder, melting point 73°–77° C.

c. (4-Amino-5-methylisoxazol-3-yl)-2-(trifluoromethyl)-phenylmethanone

A solution of (5-methyl-4-nitroisoxazol-3-yl)-2-(trifluoromethyl)phenylmethanone of Example IXb (126 g, 0.42 moles) in tetrahydrofuran (THF) (300 ml) was added to a mixture of $SnCl_2.2H_2O$ (294 g, 1.3 moles) in concentrated hydrochloric acid (400 ml) and THF (300 ml) at 15° C. The reaction mixture was stirred at room temperature overnight (about 16 hours), and poured into cold 10% sodium hydroxide with stirring. The organic phase was separated and the aqueous was extracted with ethyl acetate. The organics were combined, washed with saturated sodium chloride dried with sodium sulfate and evaporated to give 97 g of an oil. The residue was flash chromatographed (20% ethyl acetate:hexane) to yield 69 g (61%) of an oil. An analytical sample was prepared by flash chromatography (20% ethyl acetate:hexane) of 3.4 g to yield 3.0 g (54%) of an oil.

ANALYSIS Calculated for $C_{12}H_9F_3N_2O_2$: 53.34%C; 3.36%H; 10.36%N; Found: 53.20%C; 3.41%H; 10.08%N.

d. N-[3-(2-Trifluoromethylbenzoyl)-5-methylisoxazol-4-yl]-bromoacetamide

Bromoacetyl bromide (53 g, 265 mmoles) was added slowly to a mixture of (4-amino-5-methyl-isoxazoyl-3-yl)-2-(trifluoromethyl) phenylmethanone of Example IXc (65g, 241 mmoles) in dichloromethane (500 ml) with 2N sodium carbonate (250 ml) and saturated sodium bicarbonate (250 ml) at 10° C. After stirring for 1 hour, the mixture was diluted with dichloromethane (400 ml) and water (400 ml). The organics were washed with water, saturated sodium chloride, dried (sodium sulfate) and evaporated to give 86 g of a solid. The residue (3.0 g) was flash chromatographed (25% ethyl acetate:hexane) to yield 2.4 g (74%) of a solid, melting point 103°–106° C.

ANALYSIS Calculated for $C_{14}H_{10}BrF_3N_2O_3$: 43.11%C; 2.59%H; 7.18%N; Found: 43.49%C; 2.66%H; 7.05%N.

e. 3-Methyl-8-[2-(trifluoromethyl)phenyl]isoxazolo[4,3-e][1,4]-diazepin-5-one

A solution of N-[3-(2-(trifluoromethyl)benzoyl)-5-methylisoxazol-4-yl]bromoacetamide of Example IXd (83.0 g, 213 mmoles) in tetrahydrofuran (200 ml) was added to a solution of ammonia (15% w/v) in methanol (1800 ml) at −60° C. The cooling bath was removed and stirring continued at room temperature overnight (about 16 hours). Concentration gave a residue that was dissolved in methanol (1000 ml) and acetic acid (30 ml). The mixture was refluxed for 6 hours and concentrated in vacuo. The residue was poured into dilute sodium bicarbonate, extracted with ethyl acetate, dried with sodium sulfate and evaporated to a solid. The material (74 g) was flash chromatographed (50% ethyl acetate:hexane) to yield 34 g of a solid. Recrystallization of 8.0 g from ethanol (100 ml) yielded 4.2 g (27%) of crystals, melting point 218°–219° C.

Analysis Calculated for $C_{14}H_{10}F_3N_3O_2$: 54.37% C; 3.27% H; 13.58% N; Found: 54.49% C; 3.63% H; 13.68% N.

EXAMPLE X 3,4-Dimethyl-8-[2-(trifluoromethyl)phenyl]isoxazolo[4,3-e]-[1,4]diazepin-5-one A solution of 3-methyl-8-[2-(trifluoromethyl)phenyl]-isoxazolo[4,3-e][1,4]diazepin-5-one of Example IXe (6.2 g, 20 mmoles) in dimethylformamide (DMF) (50 ml) was added to a suspension of hexane-washed sodium hydride (0.86 g, 18 mmoles, 50% oil dispersion) in DMF (50 ml) at 5° C. After warming to 20° C., methyl iodide (1.4 ml, 22 mmoles) was added. The resulting solution was poured into dilute sodium bicarbonate and extracted with ethyl acetate. The organic solution was washed with water, saturated sodium chloride and dried with sodium sulfate. Concentration gave a solid (6.8 g) which was chromatographed by high pressure liquid chromatography (HPLC) (12% ethyl acetate:dichloromethane) to yield 4.5 g (70%) of a solid, melting point 115°–116.5° C.

Analysis Calculated for $C_{15}H_{12}F_3N_3O_2$: 55.73% C; 3.75% H; 12.99% N; Found: 55.65% C; 3.96% H; 12.96% N.

EXAMPLE XI 4-(2-Diethylaminoethyl)-3-methyl-8-[2-(trifluoromethyl)phenyl]-isoxazolo[4,3-e][1,4]diazepin-5-one A solution of 3-methyl-8-[2-(trifluoromethyl)phenyl]isoxazolo[4,3-e][1,4]diazepin-5-one of Example IXe (4.6 g, 15 mmoles) in dimethylformamide (DMF) (40 ml) was added to a suspension of hexane-washed sodium hydride (0.65 g, 13.5 mmoles, 50% oil dispersion) in DMF (40 ml) at 5° C. After warming to 20° C., 2-diethylaminoethyl chloride (3.0 g, 22 mmoles) was added dropwise. The reaction solution was stirred overnight (about 16 hours) at room temperature and poured into dilute sodium bicarbonate. The mixture was extracted with ethyl acetate, the organic extract was washed with water, saturated sodium chloride and dried with sodium sulfate. Concentration gave an oily residue (5.6 g) which was flash chromatographed (5% methanol:dichloromethane) to yield 4.0 g (66%) of an oil.

Analysis: Calculated for $C_{20}H_{23}F_3N_4O_2$: 54.95% C; 5.20% H; 10.68% N; Found: 54.93% C; 5.24% H; 10.68% N.

EXAMPLE XII

3-Methyl-4-(2-propynyl)-8-[2-(trifluoromethyl)phenyl]-isoxazolo[4,3-e][1,4]diazepin-5-one A solution of 3-methyl-8-[2-(trifluoromethyl)phenyl]-isoxazolo[4,3-e][1,4]diazepin-5-one of Example IXe (4.6 g, 15 mmoles) in dimethylformamide (DMF) (40 ml) was added to a suspension of hexane-washed sodium hydride (0.65 g, 13.5 mmoles, 50% oil dispersion) in DMF (30 ml) at 5° C. After warming to 20° C., propargyl bromide (2.4 g, 20 mmoles) was added. The reaction solution was stirred 1 hour and then poured into dilute sodium bicarbonate and extracted with ethyl acetate. The organic solution was washed with water, saturated sodium chloride, and dried (sodium sulfate). Concentration gave a sticky gum (5.3 g) which was chromatographed by high pressure liquid chromatography (HPLC) (6% ethyl acetate:dichloromethane) to yield 2.1 g (40%) of a resin.

Analysis: Calculated for $C_{17}H_{12}F_3N_3O_2$: 58.79% C; 3.49% H; 12.09% N; Found: 58.61% C; 3.62% H; 12.09% N.

EXAMPLE XIII a. 2,6-Difluorophenylglyoxylohydroxamyl bromide

A solution of bromine (4.1 ml, 80 mmoles) in dichloromethane (6 ml) was added dropwise to a solution of 2,6-difluoroacetophenone (12.4 g, 80 mmoles) in anhydrous diethyl ether (100 ml). the reaction solution was evaporated and the resulting liquid was dissolved in tetrahydrofuran (150 ml) and methyl sulfide (9 ml, 120 mmoles) was added. The mixture was allowed to stand at room temperature for 6 days (approximately 144 hours). The crystals were filtered to yield 8.9 g (38%) of dimethyl-2,6-difluorophenacylsulfonium bromide. A mixture of the sulfonium salt (8.9 g) and isopropyl nitrate (6.4 ml, 60 mmoles) was stirred in dichloromethane (80 ml) for 7 days (approximately 168 hours) at room temperature. The volatiles were evaporated and the residue was dissolved in diethyl ether (250 ml). The organic solution was washed 4 times with 100 ml portions of water, saturated sodium chloride, dried (sodium sulfate), and evaporated to give 6.8 g of a solid. Recrystallization from carbon tetrachloride (250 ml) gave 4.9 g (23%) of crystals, melting point 138°–140° C.

Analysis: Calculated for $C_8H_4BrF_2NO_2$: 36.39% C; 1.53% H; 5.30% N; Found: 36.22% C; 1.50% H; 5.28% N.

b.
(5-Methyl-4-nitroisoxazol-3-yl)-2,6-difluorophenylmethanone

To a solution of nitroacetone (26.4 g, 256 mmoles) in tetrahydrofuran (THF) (600 ml) at 5° C. was added triethylamine (34.6 ml, 250 mmoles) dropwise. A solution of 2,6-difluorophenylglyoxylohydroxamyl bromide of Example XIIIa (65.8 g, 250 mmoles) in THF (250 ml) was added at 5° C. over 1 hour. The reaction was stirred at room temperature overnight (approximately 16 hours). The mixture was filtered, the salts were washed with ethyl acetate and the organics were combined and evaporated to give an oil (77 g). The residue was flash chromatographed (20% ethyl acetate:hexane) to yield 38 g (57%) of an oil that solidified on standing. Recrystallization from ethanol (150 ml) gave 17.0 g (25%) of crystals, melting point 69°–72° C.

Analysis Calculated for $C_{11}H_6F_2N_2O_4$: 49.26% C; 2.26% H; 10.44% N; Found: 49.43% C; 2.30% H; 10.50% N.

c.
(4-Amino-5-methylisoxazol-3-yl)-2,6-difluorophenylmethanone

A solution of (5-methyl-4-nitroisoxazol-3-yl)-2,6-difluorophenylmethanone of Example XIIIb (82.6 g, 308 mmoles) in tetrahydrofuran (THF) (200 ml) was added to a mixture of $SnCl_2.2H_2O$ (210 g, 938 mmoles) in concentrated hydrochloric acid (400 ml) and THF (400 ml) at 15° C. The reaction mixture was stirred at room temperature for 3 hours and poured into a mixture of 50% sodium hydroxide (700 g) and ice with stirring. The organic phase was separated and the aqueous was extracted with ethyl acetate. The organics were combined, washed with saturated sodium chloride, dried (sodium sulfate), and evaporated to give 63 g of an oil. The residue was flash chromatographed (20% ethyl acetate:hexane) to yield 51 g (70%) of an oil that crystallized on standing. The amine (4.0 g) was chromatographed by high pressure liquid chromatography (20% ethyl acetate:hexane) to yield 2.3 g (40%) of a solid, melting point 63°–68° C.

Analysis: Calculated for $C_{11}H_8F_2N_2O_2$: 55.46% C; 3.39% H; 11.76% N; Found: 55.42% C; 3.41% H; 11.64% N.

d.
N-[3-(2,6-Difluorobenzoyl)-5-methylisoxazol-4-yl]bromoacetamide

Bromoacetyl bromide (44 g, 222 mmoles) was added slowly to a mixture of (4-amino-5-methylisoxazol-3-yl)-

2,6-difluorophenylmethanone of Example XIIIc (48 g, 202 mmoles) in dichloromethane (400 ml) with 2N sodium carbonate (125 ml) and saturated sodium chloride, dried (sodium sulfate) and evaporated to give 72 g of an oil. The residue (3.0 g) was flash chromatographed (25% ethyl acetate:hexane) to yield 2.3 g (77%) of a solid, melting point 76°–80° C.

Analysis: Calculated for $C_{13}H_9BrF_2N_2O_3$: 43.48% C; 2.53% H; 7.80% N; Found: 43.63% C; 2.52% H; 7.74% N.

e.

3-Methyl-8-(2,6-difluorophenyl)isoxazolo[4,3-e][1,4]-diazepin-5-one

A solution of N-[3-(2,6-difluorobenzoyl)-5-methylisoxazol-4-yl]bromoacetamide of Example XIIId (69 g, 193 mmoles) in tetrahydrofuran (170 ml) was added to a solution of ammonia (15% w/v) in methanol (1600 ml) at −60° C. The cooling bath was removed and stirring continued at room temperature overnight (approximately 16 hours). Concentration gave a residue that was dissolved in methanol (800 ml) and acetic acid (25 ml). The mixture was refluxed for 6 hours and concentrated in vacuo. The residue was poured into dilute sodium bicarbonate, extracted with ethyl acetate, the organics washed with saturated sodium chloride, dried (sodium sulfate) and evaporated to give a residue. The material (58 g) was flash chromatographed (50% ethyl acetate:hexane) to yield 11.1 g of a solid. Recrystallization of 3.5 g from 1-propanol (100 ml) yielded 2.0 g (12%) of a crystalline powder, melting point 258°–260° C.

Analysis: Calculated for $C_{13}H_9F_2N_3O_2$: 56.32% C; 3.28% H; 14.15% N; Found: 56.14% C; 3.24% H; 15.03% N.

EXAMPLE XIV 3,4-Dimethyl-8-(2,6-difluorophenyl)isoxazolo[4,3-e][1,4]-diazepin-5-one A solution of 3-methyl-8-(2,6-difluorophenyl)-isoxazolo-[4,3-e][1,4]diazepin-5-one of Example XIIIe (6.3 g 22.7 mmoles) in dimethylformamide (DMF) (45 ml) was added to a suspension of hexane-washed sodium hydride (0.98 g, 20.4 mmoles, 50 % oil dispersion) in DMF (50 ml) at 5° C. After warming to 20° C., methyl iodide (1.55 ml, 25 mmoles) was added dropwise. The resulting solution was poured into dilute sodium bicarbonate and extracted with ethyl acetate. The organic solution was washed with water, saturated sodium chloride, and dried (sodium sulfate). Concentration gave a solid (6.5 g) which was chromatographed by high pressure liquid chromatography (HPLC) (12% ethyl acetate:dichloromethane) to yield 3.5 g of a solid. Recrystallization from ethanol (70 ml) gave 2.6 g (39%) of a crystalline powder, melting point 190.0°–190.5° C.

Analysis: Calculated for $C_{14}H_{11}F_2N_3O_2$: 57.73% C; 3.81% H; 14.42% N; Found: 57.84% C; 3.89% H; 14.56% N.

We claim:

1. A compound having the formula

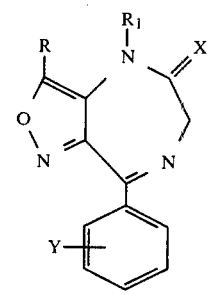

wherein R is lower alkyl; $R_1$ is hydrogen, propargyl, amino lower alkyl and lower alkyl; X is oxygen and sulfur; and Y is halogen, trifluoromethyl, lower alkyl, lower alkoxy and hydrogen; and the pharmaceutically acceptable acid addition salts thereof.

2. The compound as defined in claim 1 wherein R is $CH_3$.

3. The compound as defined in claim 1 wherein $R_1$ is hydrogen.

4. The compound as defined in claim 1 wherein $R_1$ is $CH_3$.

5. The compound as defined in claim 1 wherein $R_1$ is diethylaminoethyl.

6. The compound as defined in claim 1 which is 4-(2-Diethylaminoethyl)-3-methyl-8-[2-(trifluoromethyl)-phenyl]isoxazolo[4,3-e][1,4]diazepin-5-one or a pharmaceutically acceptable salt thereof.

7. The compound as defined in claim 1 which is 3,4-Dimethyl-8-[2-(trifluoromethyl)phenyl]isoxazolo[4,3-e][1,4]diazepin-5-one or a pharmaceutically acceptable salt thereof.

8. The compound as defined in claim 1 which is 3-Methyl-8-[2-(trifluoromethyl)phenyl]isoxazolo[4,3-e][1,4]diazepin-5-one or a pharmaceutically acceptable salt thereof.

9. The compound as defined in claim 1 which is 4-(2-Diethylaminoethyl)-3-methyl-8-(2-fluorophenyl)isoxazolo-[4,3-e][1,4]-diazepin-5-one or a pharmaceutically acceptable salt thereof.

10. The compound as defined in claim 1 which is 3-Methyl-8-(2-fluorophenyl)isoxazolo[4,3-e][1,4]diazepin-5-one or a pharmaceutically acceptable salt thereof.

11. The compound as defined in claim 1 which is 3,4-Dimethyl-8-(2-fluorophenyl)isoxazolo[4,3-e][1,4]diazepin-5-one or a pharmaceutically acceptable salt thereof.

12. The compound as defined in claim 1 which is 3,4-Dimethyl-8-(4-chlorophenyl)isoxazolo[4,3-e][1,4]diazepin-5-one or a pharmaceutically acceptable salt thereof.

13. The compound as defined in claim 1 which is 3,4-Dimethyl-8-(2-chlorophenyl)isoxazolo[4,3-e][1,4]diazepin-5-one or a pharmaceutically acceptable salt thereof.

14. The compound as defined in claim 1 which is 3-Methyl-8-(2-chlorophenyl)isoxazolo[4,3-e][1,4]diazepin-5-one or pharmaceutically acceptable salt thereof.

15. The compound as defined in claim 1 which is 3,4-Dimethyl-8-phenylisoxazolo[4,3-e][1,4]diazepin-5-one or a pharmaceutically acceptable salt thereof.

16. The compound as defined in claim 1 which is 3-Methyl-8-phenylisoxazolo[4,3-e][1,4]diazepin-5-one or a pharmaceutically acceptable salt thereof.

17. The compound as defined in claim 1 which is 3-Methyl-8-(2,6-difluorophenyl)isoxazolo[4,3-e][1,4]diazepin-5-one or a pharmaceutically acceptable salt thereof.

18. The compound as defined in claim 1 which is 3,4-Dimethyl-8-(2,6-difluorophenyl)isoxazolo[4,3-e][1,4]-diazepin-5-one or a pharmaceutically acceptable salt thereof.

19. The compound as defined in claim 1 which is 3-Methyl-4-(2-propynyl)-8-[2-(trifluoromethyl)phenyl-]isoxazolo-or a pharmaceutically acceptable salt thereof.

20. A compound having the formula

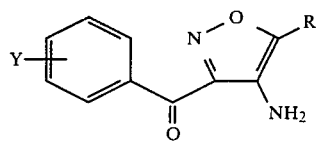

wherein Y is halogen, trifluoromethyl, lower alkyl, lower alkoxy and hydrogen; and R is lower alkyl.

21. The compound as defined in claim 20 in which R is $CH_3$.

22. The compound as defined in claim 20 in which Y is chlorine.

23. The compound as defined in claim 20 in which Y is fluorine.

24. The compound as defined in claim 20 in which Y is trifluoromethyl.

25. The compound as defined in claim 20 in which Y is hydrogen.

26. An anxiolytic composition which comprises an effective anxiolytic amount of a compound of the formula

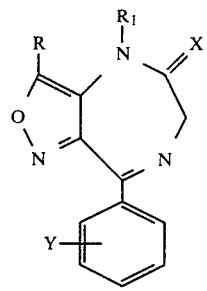

wherein R is lower alkyl; $R_1$ is hydrogen, propargyl, amino lower alkyl and lower alkyl; X is oxygen and sulfur; and Y is halogen, trifluoromethyl, lower alkyl, lower alkoxy and hydrogen; and the pharmaceutically acceptable acid addition salts thereof.

27. The composition as defined in claim 26 wherein R is $CH_3$.

28. The composition as defined in claim 26 wherein $R_1$ is hydrogen.

29. The composition as defined in claim 26 where $R_1$ is $CH_3$.

30. The composition as defined in claim 26 wherein $R_1$ is diethylaminoethyl.

31. The composition defined in claim 26 which comprises 4-(2-Diethylaminoethyl)-3-methyl-8-[2-(trifluoromethyl)phenyl]-isoxazolo[4,3-e][1,4]diazepin-5-one or a pharmaceutically acceptable salt thereof.

32. The composition defined in claim 26 which comprises 3,4-Dimethyl-8-[2-(trifluoromethyl)phenyl]isoxazolo[4,3-e]-[1,4]diazepin-5-one or a pharmaceutically acceptable salt thereof.

33. The composition defined in claim 26 which comprises 3-Methyl-8-[2-(trifluoromethyl)phenyl]isoxazolo[4,3-e][1,4]-diazepin-5-one or a pharmaceutically acceptable salt thereof.

34. The composition defined in claim 26 which comprises 4-(2-Diethylaminoethyl)-3-methyl-8-(2-fluorophenyl)isoxazolo-[4,3-e][1,4]diazepin-5-one or a pharmaceutically acceptable salt thereof.

35. The composition defined in claim 26 which comprises 3-Methyl-8-(2-fluorophenyl)isoxazolo[4,3-e][1,4]diazepin-5-one or a pharmaceutically acceptable salt thereof.

36. The composition defined in claim 26 which comprises 3,4-Dimethyl-8-(2-fluorophenyl)isoxazolo[4,3-e][1,4]diazepin-5-one or a pharmaceutically acceptable salt thereof.

37. The composition defined in claim 26 which comprises 3,4-Dimethyl-8-(4-chlorophenyl)isoxazolo[4,3-e][1,4]diazepin-5-one or a pharmaceutically acceptable salt thereof.

38. The composition defined in claim 26 which comprises 3,4-Dimethyl-8-(2-chlorophenyl)isoxazolo[4,3-e][1,4]diazepin-5-one or a pharmaceutically acceptable salt thereof.

39. The composition defined in claim 26 which comprises 3-Methyl-8-(2-chlorophenyl)isoxazolo[4,3-e][1,49 diazepin-5-one or a pharmaceutically acceptable salt thereof.

40. The composition defined in claim 26 which comprises 3,4-Dimethyl-8-phenylisoxazolo[4,3-e][1,4]diazepin-5-one or a pharmaceutically acceptable salt thereof.

41. The composition defined in claim 26 which comprises 3-Methyl-8-phenylisoxazolo[4,3-e][1,4]diazepin-5-one or a pharmaceutically acceptable salt thereof.

42. The composition defined in claim 26 which comprises 3-Methyl-8-(2,6-difluorophenyl)isoxazolo[4,3-e][1,4]diazepin-5-one or a pharmaceutically acceptable salt thereof.

43. The composition defined in claim 26 which comprises 3,4-Dimethyl-8-(2,6-difluorophenyl)isoxazolo[4,3-e][1,4]diazepin-5-one or a pharmaceutically acceptable salt thereof.

44. The composition defined in claim 26 which comprises 3-Methyl-4-(2-propynyl)-8-[2-(trifluoromethyl)-phenyl]isoxazolo-[4,3-e][1,4]diazepin-5-one or a pharmaceutically acceptable salt thereof.

45. An anticonvulsant composition which comprises an effective anticonvulsant amount of a compound of the formula

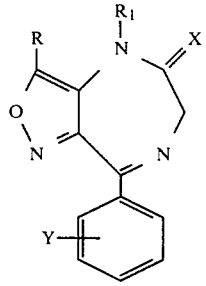

wherein R is lower alkyl; $R_1$ is hydrogen, propargyl, amino lower alkyl and lower alkyl; X is oxygen and sulfur; and Y is halogen, trifluoromethyl, lower alkyl, lower alkoxy and hydrogen; and the pharmaceutically acceptable acid addition salts thereof.

46. The composition as defined in claim 45 wherein R is CH₃.

47. The composition as defined in claim 45 wherein R₁ is hydrogen.

48. The composition as defined in claim 45 wherein R₁ is CH₃.

49. The composition as defined in claim 45 wherein R₁ is diethylaminoethyl.

50. The composition as defined in claim 45 which comprises 4-(2-Diethylaminoethyl)-3-methyl-8-[2-(trifluoromethyl)phenyl]-isoxazolo[4,3-e][1,4]diazepin-5-one or a pharmaceutically acceptable salt thereof.

51. The composition as defined in claim 45 which comprises 3,4-Dimethyl-8-[2-(trifluoromethyl)phenyl]isoxazolo[4,3-e][1,4]-diazepin-5-one or a pharmaceutically acceptable salt thereof.

52. The composition as defined in claim 45 which comprises 3-Methyl-8-[2-(trifluoromethyl)phenyl]isoxazolo[4,3-e][1,4]-diazepin-5-one or a pharmaceutically acceptable salt thereof.

53. The composition as defined in claim 45 which comprises 4-(2-Diethylaminoethyl)-3-methyl-8-(2-fluorophenyl)isoxazolo[4,3-e][1,4]diazepin-5-one or a pharmaceutically acceptable salt thereof.

54. The composition as defined in claim 45 which comprises 3-Methyl-8-(2-fluorophenyl)isoxazolo[4,3-e][1,4]-diazepin-5-one or a pharmaceutically acceptable salt thereof.

55. The composition as defined in claim 45 which comprises 3,4-Dimethyl-8-(2-fluorophenyl)isoxazolo[4,3-e][1,4]diazepin-5-one or a pharmaceutically acceptable salt thereof.

56. The composition as defined in claim 45 which comprises 3,4-Dimethyl-8-(4-chlorophenyl)isoxazolo[4,3-e][1,4]diazepin-5-one or a pharmaceutically acceptable salt thereof.

57. The composition as defined in claim 45 which comprises 3,4-Dimethyl-8-(2-chlorophenyl)isoxazolo[4,3-e][1,4]diazepin-5-one or a pharmaceutically acceptable salt thereof.

58. The composition as defined in claim 45 which comprises 3-Methyl-8-(2-chlorophenyl)isoxazolo[4,3-e][1,4]diazepin-5-one or a pharmaceutically acceptable salt thereof.

59. The composition as defined in claim 45 which comprises 3,4-Dimethyl-8-phenylisoxazolo[4,3-e][1,4]diazepin-5-one or a pharmaceutically acceptable salt thereof.

60. The composition as described in claim 45 which comprises 3-Methyl-8-phenylisoxazolo[4,3-e][1,4]diazepin-5-one or a pharmaceutically acceptable salt thereof.

61. The composition as defined in claim 45 which comprises 3-Methyl-8-(2,6-difluorophenyl)isoxazolo[4,3-e][1,4]diazepin-5-one or a pharmaceutically acceptable salt thereof.

62. The composition as defined in claim 45 which comprises 3,4-Dimethyl-8-(2,6-difluorophenyl)isoxazolo[4,3-e][1,4]diazepin-5-one or a pharmaceutically acceptable salt thereof.

63. The composition as defined in claim 45 which comprises 3-Methyl-4-(2-propynyl)-8-[2-(trifluoromethyl)phenyl]isoxazolo-[4,3-e][1,4]diazepin-5-one or a pharmaceutically acceptable salt thereof.

64. A method of reducing anxiety in a patient in need thereof which comprises administering to a patient an effective anxiolytic amount of a compound of the formula

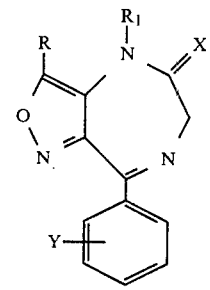

wherein R is a lower alkyl; R₁ is hydrogen, propargyl, amino lower alkyl and lower alkyl; X is oxygen and sulfur; and Y is halogen, trifluoromethyl, lower alkyl, lower alkoxy and hydrogen; and the pharmaceutically acceptable acid addition salts thereof.

65. The method as defined in claim 64 wherein R is CH₃.

66. The method as defined in claim 64 wherein R₁ is hydrogen.

67. The method as defined in claim 64 wherein R₁ is CH₃.

68. The method as defined in claim 64 wherein R₁ is diethylaminoethyl.

69. A method of reducing convulsions in a patient which comprises administering to a patient a convulsion reducing amount of a compound of the formula

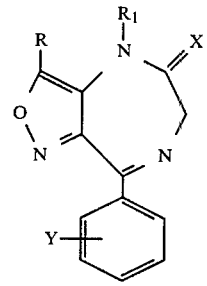

wherein R is lower alkyl; R₁ is hydrogen, propargyl, amino lower alkyl and lower alkyl; X is oxygen and sulfur; and Y is halogen, trifluoromethyl, lower alkyl, lower alkoxy and hydrogen; and the pharmaceutically acceptable acid addition salts thereof.

70. The method as defined in claim 69 wherein R is CH₃.

71. The method as defined in claim 69 wherein R₁ is hydrogen.

72. The method as defined in claim 69 wherein R₁ is CH₃.

73. The method as defined in claim 69 wherein R₁ is diethylaminoethyl.

* * * * *